(12) United States Patent
Chen et al.

(10) Patent No.: US 6,195,891 B1
(45) Date of Patent: Mar. 6, 2001

(54) METHOD FOR IDENTIFICATION AND REPAIR OF INDICATIONS IN HARDWARE

(75) Inventors: Keng N. Chen; Genfa Hu, both of Singapore (SG)

(73) Assignees: GE Aviation Service Operation; Operation Private Limited, both of (SG)

( * ) Notice: Subject to any disclaimer, the term of this patent is extended or adjusted under 35 U.S.C. 154(b) by 0 days.

(21) Appl. No.: 09/298,610

(22) Filed: Apr. 26, 1999

(51) Int. Cl.[7] .................................................. B23P 15/00
(52) U.S. Cl. ....................... 29/889.1; 29/889.7; 250/458.1
(58) Field of Search ............................ 29/889.1, 889.7, 29/402.13, 402.16, 402.18; 228/119; 250/458.1, 459.1, 461.1

(56) References Cited

U.S. PATENT DOCUMENTS

| 4,028,787 | | 6/1977 | Cretella et al. ...................... 29/156.8 |
| 4,037,961 | * | 7/1977 | Macemon ............................... 356/85 |
| 4,194,217 | * | 3/1980 | van den Bosch ..................... 356/323 |
| 4,647,199 | * | 3/1987 | Ferber et al. ....................... 250/461.1 |
| 4,697,924 | * | 10/1987 | Akiyama ............................... 356/333 |
| 5,001,353 | * | 3/1991 | Odake et al. ....................... 250/461.1 |
| 5,182,080 | * | 1/1993 | Beltran et al. ........................ 420/588 |
| 5,285,572 | * | 2/1994 | Rathi et al. .......................... 29/889.1 |
| 5,303,026 | * | 4/1994 | Strobl et al. ....................... 250/458.1 |
| 5,320,690 | * | 6/1994 | Beltran et al. ........................ 228/119 |
| 5,563,417 | | 10/1996 | Gillard et al. ..................... 250/461.1 |
| 5,569,546 | * | 10/1996 | Ferrigno et al. ..................... 29/889.1 |
| 5,902,421 | * | 5/1999 | Christy ................................. 148/528 |
| 6,049,060 | * | 4/2000 | Smashey et al. ..................... 228/119 |

FOREIGN PATENT DOCUMENTS 0159144   6/1989   (JP).

* cited by examiner

Primary Examiner—I Cuda Rosenbaum
(74) Attorney, Agent, or Firm—Andrew C. Hess; Gerry S. Gressel

(57) ABSTRACT

A method for identifying and repairing indications open to the surface of a turbine component, such as cracks or other tight crevices that may develop during turbine engine operation. The process includes cleaning the component of debris, dirt or other foreign material that may otherwise mask the presence of the indications. This is followed by applying a fluorescent penetrant to the surface of the component. Without removing the penetrant, the article is visually inspected under normal lighting conditions and repair alloy is applied as needed to areas requiring repair. Next, the article is inspected under an ultraviolet light, at which time very tight indications not otherwise detectable by the unaided eye are identified as areas requiring repair and repair alloy is applied to these additional areas, by an automatic and/or manual process. Without removing the penetrant, the article is then heated to an elevated temperature sufficient to liquify at least a portion of the repair alloy to accomplish the repair.

10 Claims, 3 Drawing Sheets

METHOD FOR IDENTIFICATION AND REPAIR OF INDICATIONS IN HARDWARE

BACKGROUND OF THE INVENTION

1. Field of the Invention

The present invention is generally directed at an improved method for detecting minute cracks in the surface of an article and automatically and/or manually repairing detected cracks, and specifically at detecting cracks in the surface of turbine engine hardware and automatically and/or manually repairing detecting such cracks with the aid of fluorescent penetrant.

2. Discussion of the Prior Art

In the course of engine operation, turbine engine hardware typically experiences minor damage as a result of engine operation. This damage can take many forms such as minor pits and cracks and may be as a result of any one of a number of conditions, such as ingestion of foreign particles, wear, erosion or fatigue. Frequently, the damage is of a minor nature, and after a repair operation, the hardware is suitable for reuse.

Currently, the articles to be repaired are visually inspected under suitable white light after cleaning so that defects or indications can be visually detected. In order to identify very fine cracks, visual inspection under magnification is conducted. As the cracks are identified by the operator, a suitable alloy in the form of a slurry is applied by the operator. The crack identification procedure and alloy application is the first step in well known repair procedures such as activated diffusion healing (ADH), partitioned alloy component healing (PACH) and brazing. After the application of the alloy, the articles are heated at elevated temperatures according to the selected procedure, ADH, PACH or brazing, which causes the alloy to flow and "heal" the defect.

After the repair procedure, the article is fluorescent penetrant inspected according to well-known procedures. These procedures require cleaning of the part, inspection of the part under an ultraviolet light, identification of any remaining defects, cleaning of the part and reapplication of the slurry for re-repair of any additionally identified defects. Of course, the problem with the procedure is that the subsequent fluorescent penetrant inspection frequently identifies defects that are not resolved or resolvable using the visual inspection techniques, with or without the aid of magnification. A process that can properly identify the defects present in the article prior to the repair cycle without adversely affecting the repair can save time, manpower, effort and energy resources if the entire repair can be completed in one cycle.

SUMMARY OF THE INVENTION

An improved method for identifying and repairing indications in the surface of articles is set forth by the present invention. The article that is to be inspected for reuse is first cleaned to remove any debris, oil, dirt or other foreign substances that could mask the indication. Fluorescent penetrant is then applied to the article. Once the penetrant is applied, the article is then visually inspected, under regular or "white" light without the aid of an ultraviolet light. This inspection reveals very large indications or defects, to which repair alloy is applied in the form of a slurry. After the manual application of the repair alloy, the article is then inspected with the aid of an ultraviolet light. The fluorescent penetrant in any fine cracks not filled with repair alloy as a result of the visual inspection under white light conditions are now revealed by the ultraviolet light. Additional repair alloy in the form of slurry is now applied to fill the additional cracks detected. The article is then subjected to the repair procedure, ADH, PACH or braze by exposing the article to an elevated temperature sufficient to cause the repair alloy to flow.

An advantage of the present invention is that all defects open to the surface of the part can be identified before repair by the combination of the inspection under white light and the inspection under ultraviolet light so that repair can be accomplished in one repair cycle. This greatly reduces the chance that defects such as cracks will be overlooked during the inspection process, as sometimes occurred in the two step inspection and repair process.

Another advantage to the present invention is that the slurry containing the braze alloy can be applied to defects such as cracks without removal of the fluorescent penetrant without adversely affecting the integrity of the repair.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE PRESENT INVENTION

The present invention is an improved process for detecting defects such as cracks that are open to the surface of an article and repairing the detected defects in the article by applying a repair alloy to the defects and heating the article to cause the repair alloy to flow and close or "heal" the defect. Articles that are typically inspected and repaired in this fashion include turbine components removed from aircraft engine service. Examples of turbine components include turbine blades, turbine vanes, turbine buckets, nozzles, combustors, and the like. Substrate materials often used in turbine parts or airfoils for aircraft engines and power generation equipment may include nickel, cobalt or iron based superalloys. The alloys may be cast or wrought superalloys. Examples of such substrates are GTD-111, GTD-222, Rene 80, Rene 41, Rene 125, Rene 77, Rene 95, Rene N5, Rene N6, Inconel 706, Inconel 718, Inconel 625, cobalt-based HS-188, cobalt-based L-605 and stainless steels. Not only are the articles made from expensive materials, they are intricate parts, further adding to their value. Because it is economically beneficial to repair these articles whenever practical in order to restore them i 0 as closely as possible to their original configuration, a number of repair procedures have been developed. However, it is important that these repairs detect defects in the articles so that they can be restored to their original configuration.

Figure 1:
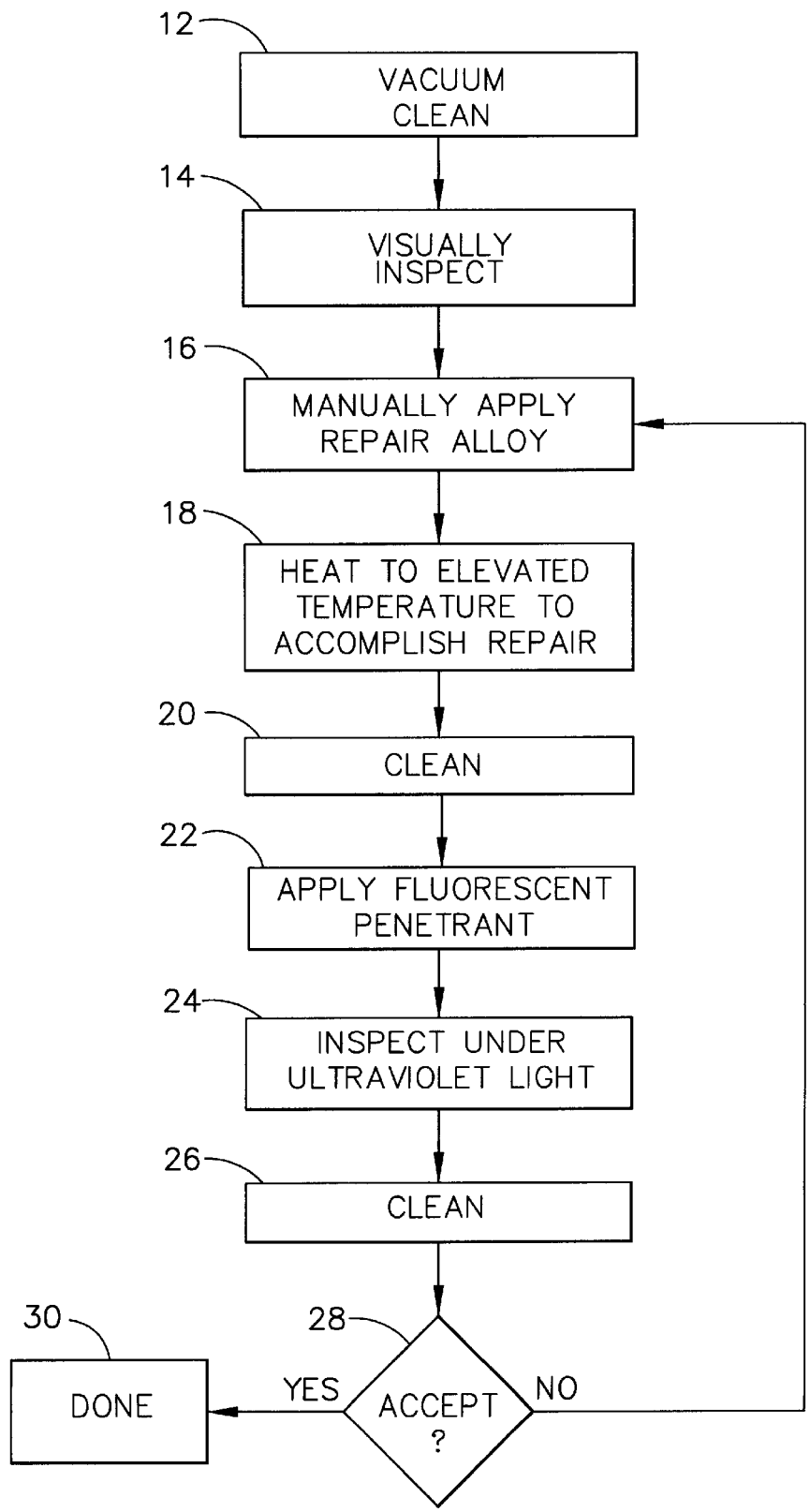
FIG. 1 is a flow chart of the prior art process for preparing airfoils.

Prior art repair procedures for repairing turbine components such as set forth in FIG. 1 have been developed that include multiple inspection and repair cycles. Such repair procedures include ADH, PACH and brazing. Each of these repair procedures involves manual application of a repair alloy to regions of a turbine component identified as requiring repair, 16, followed by placing the turbine component in an elevated temperature environment, 18, sufficiently high to at least partially liquify the repair alloy.

Figure 2:
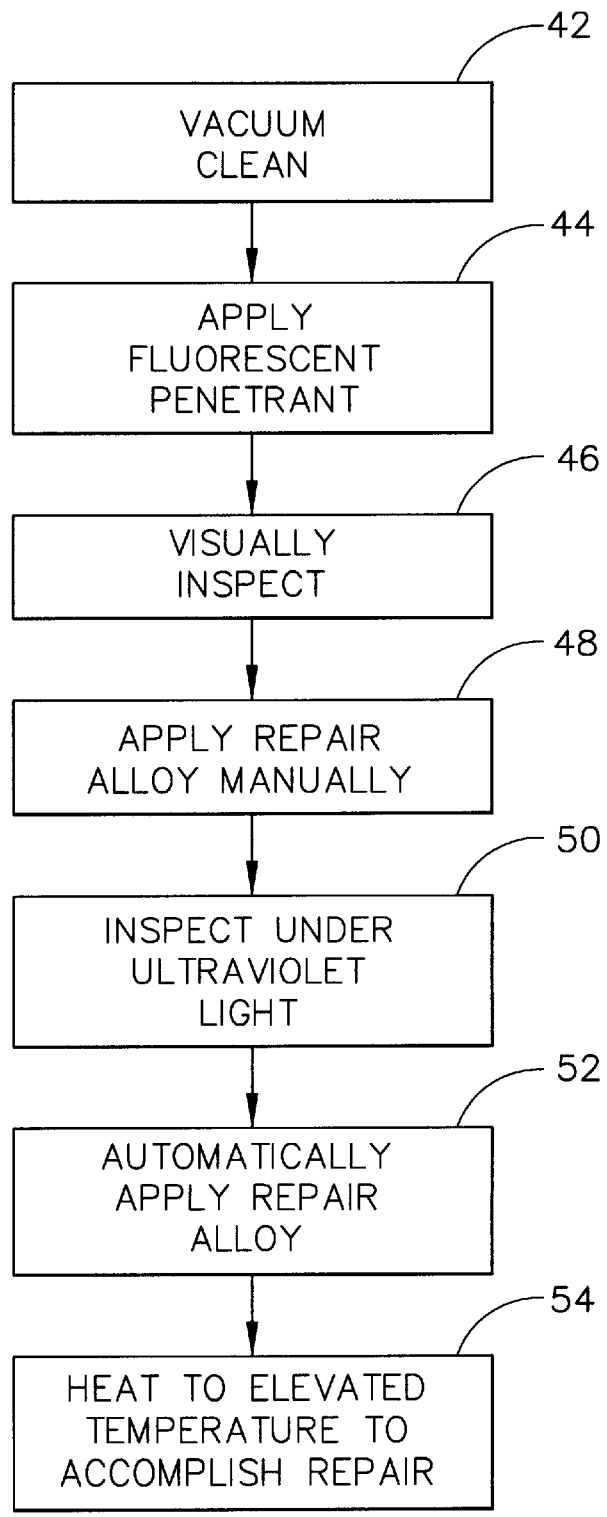
FIG. 2 is a flow chart of the process of the present invention.

The repair procedures of the present invention are set forth in FIG. 2. FIG. 2 is a flow chart of that outlines the steps for repairing an article in accordance with the present invention. The present invention provides improvements over the prior art processes in that all of the indications open to the surface are identified in initial inspections, 44 and 50, that are performed before the airfoil is subjected to the elevated temperature environment 54. The process of the present invention identifies all relevant indications during two inspections, a first visual inspection 46 that is performed under white light or conventional lighting and a second inspection that is performed under ultraviolet light 50. The first visual inspection 46 identifies very broad indications that are open to the surface that might not readily show up under an ultraviolet light, while the second inspection 50 identifies, using standard penetrant principles, very fine cracks that may not be observable under white light conditions even under high magnification.

The process of the present invention further deviates from standard practice in that repair alloy is applied to the area requiring repairs without first cleaning the fluorescent penetrant from the indication. The repair alloy is applied to the area identified as requiring repair by applying the alloy directly into the indication and over the fluorescent penetrant, without first cleaning the penetrant from the indication. This practice deviates from the conventional practices when utilizing penetrants. This practice always included a subsequent cleaning operation prior to attempting a repair, since any trapped penetrant could produce an inadequate repair. However, the process of the present invention does not require a cleaning step to remove penetrant prior to subjecting the component to the step of heating to an elevated temperature in order to accomplish the repair 54 by partially liquefying the repair alloy. The repair process of the present invention does not trap any remaining fluorescent penetrant in a manner that leads to an inadequate repair. All repairs made by the process of the present invention have been satisfactory, so that the component could be reused after repair and without the need for a subsequent repair cycle.

The vacuum cleaning 42 of the part removes contamination from the surface of the component under repair. This contamination includes organic impurities and dirt such as sand, volcanic ash, fly ash, cement, runway dust, substrate impurities, fuel and air sources, oxidation products from engine components, and the like. This is an important step since any indications such as cracks that are open to the surface should be repaired, and this contamination can block the pathway to the surface. Fluorescent penetrant is then applied to the surface of the part 44 by conventional methods such as by dipping or spraying, and the penetrant is given a brief period of time, 3 to 15 minutes for example, to penetrate into any tight openings by capillary action. Excess penetrant is removed from the surface of the component by wiping or by spraying the surface of the component in a manner well known to those skilled in the art. The component, typically an airfoil, is then inspected under white light conditions 46, typically at a preselected lighting level that can be verified by a light meter. This inspection discloses very broad shallow indications that may or may not be susceptible to disclosure under the ultraviolet light. In a typical repair sequence, repair alloy is manually 48 applied to those regions of the airfoil identified in the white light inspection step 46 without removal of any fluorescent penetrant that may be present. The airfoil is then inspected under an ultraviolet light 50 where tight indications such as fine cracks otherwise not readily observable to the unaided eye are disclosed. Once identified, repair alloy is applied, 52, either automatically or manually, without removing the fluorescent penetrant from the tight indication. The article is then heated to an elevated temperature, typically above about 1800° F., to accomplish the repair by causing at least a portion of the repair alloy to be liquified. However, fluorescent penetrant is not trapped in the indication so as to cause an unacceptable repair.

Figure 3:
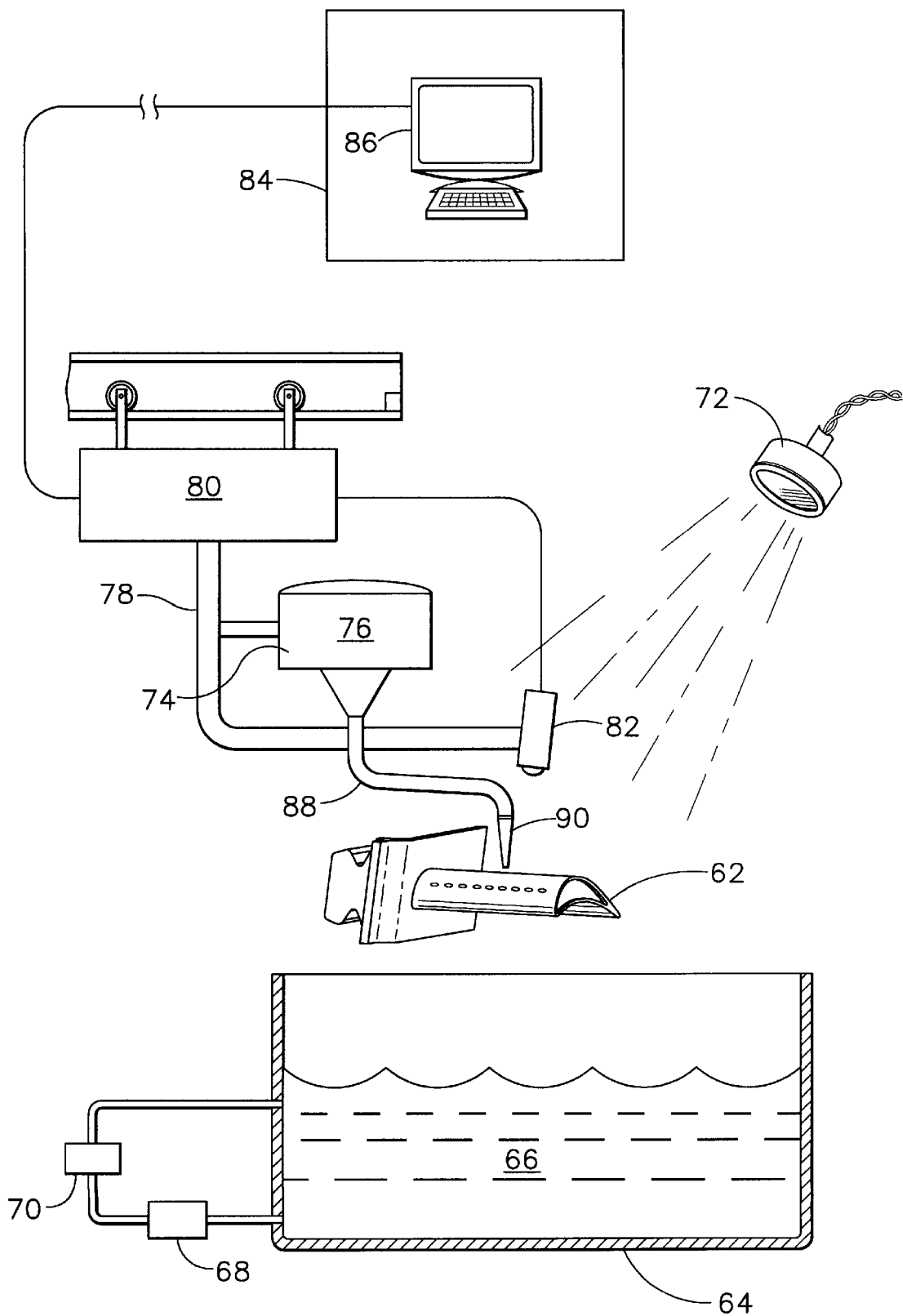
FIG. 3 is a schematic of a preferred embodiment of the present invention.

Referring now to FIG. 3, which is an illustration of the equipment used in a preferred method of practicing the present invention, an airfoil 62 is positioned proximate to a reservoir 64 that holds a volume of fluorescent penetrant 66. The airfoil may be positioned in a fixture (not shown that may hold a plurality of airfoils. Attached to reservoir 64 is a circulating pump 68 and a filter 70 to remove any impurities from penetrant 66. Penetrant may be applied to the airfoil by dipping or by spraying, both being equivalent methods, and excess penetrant can drain back into reservoir 64. Excess penetrant can be removed from the airfoil by wiping the airfoil, or, to increase the processing speed, by moving article to a separate location and either lightly spraying or quickly dipping the article in a solution that will not penetrate the tight crack-like indications. Typically, a water spray is utilized.

As illustrated, positioned over the airfoil 62 is a lamp 72 that contains at least an ultraviolet light. It may also house a regular light, although the lighting may be located in different lamps and in different positions. It will be understood that lamp 72 may be located in a region adjacent reservoir 64, and after application of penetrant 66, the fixture holding at least one airfoil 62 can be moved to this adjacent region for the subsequent operations, such as removal of excess penetrant. A container 74 that holds a quantity of repair material 76 in the form of a slurry is shown attached to a rigid arm 78, which in turn is attached to a truck 80. The material 76 in the form of a slurry can be applied to airfoil 62 through tube 88 by activating dispensing means, not shown, in the form of a mechanical device or alternative and equivalently, by application of compressed air to force a preselected amount of material through tube 88 to be deposited by nozzle 90 onto a preselected portion of airfoil 62. The truck and the arm have at least two degrees of freedom. For simplicity, truck 80 and arm 78 are shown as having the capability of moving in the X-Y plane in FIG. 3, so that material 76 can be deposited from container 74 onto airfoil 62.

Also attached to arm 78 is a television camera 82, which is focused on airfoil 62. This camera 82 provides visual feedback to a control room 84 where the image from airfoil 62 is displayed on screen 86. From control room 84, the truck 80, arm 78 and material 76 in container 74 can be remotely manipulated to apply material 76 onto any indications on the surface of airfoil 62 that are highlighted by the fluorescent penetrant as it is illuminated by ultraviolet light 72. These highlighted areas are the preselected portions of the airfoil onto which material 76 in the form of a slurry is to be deposited. In the preferred embodiment, camera 82 is a CCD camera, which provides feedback to a vision system (not shown) in control room 86. This vision system is programmed so that it can detect the bright areas requiring repair on the surface of airfoil 62 that are illuminated when the ultraviolet light irradiates any residual penetrant. Vision systems with such capabilities are well known. The vision system can then provide feedback to the controls for arm 78 and truck 80, so that truck 80 and arm 78 can be automatically positioned over preselected portions of airfoil 62. Once positioned appropriately, dispensing means can be activated in conjunction with the positioning capabilities of the device so that material 76 in slurry form from container 74 can be dispensed through nozzle 90 onto airfoil 62.

This ability of the present invention to automatically detect and dispense slurry onto the airfoil in regions requiring repair is another novel aspect of the present invention not heretofore capable of being practiced. Since the fluorescent penetrant is not removed from airfoil 62, the present invention permits material 76 in the form of slurry to be deposited directly onto areas requiring repair, as these areas are highlighted by the penetrant. Thus, not only is the repair accomplished faster by elimination of additional repair cycles, the operation can be performed automatically, which adds speed and eliminates variables such as operator error or operator judgement and discretion from the repair procedure.

Although the present invention has been described in connection with specific examples and embodiments, those skilled in the art will recognize that the present invention is capable of other variations and modifications within its scope. These examples and embodiments are intended as typical of, rather than in any way limiting on, the scope of the present invention as presented in the appended claims.

What is claimed is:

1. A method for repairing indications open to a surface of an article, comprising the steps of:

cleaning a surface of the article;

applying a fluorescent penetrant to the surface of the article;

visually inspecting the surface of the article under normal lighting conditions at preselected levels of white light to detect areas requiring repair; then applying repair alloy to the article in preselected areas requiring repair as identified by visual inspection; then inspecting the surface of the article under ultraviolet light at preselected levels to detect areas requiring repair detectable by the fluorescent penetrant and not readily detectable by visual inspection; then applying a repair alloy to the article in preselected areas requiring repair as identified by fluorescent penetrant inspection under ultraviolet light and visual inspection under white light; and placing the article in an elevated temperature atmosphere sufficient to liquify at least a portion of the repair alloy, so that the repair alloy flows into the areas requiring repair.

2. The method of claim 1 wherein the article is a turbine engine component.

3. The method of claim 2 wherein the article is an engine component selected from the group consisting of turbine blades, turbine vanes, turbine buckets, nozzles, and combustors.

4. The method of claim 2 wherein the alloy is applied to the surface of the component after visual inspection by a manual application.

5. The method of claim 2 wherein the alloy is applied to the surface of the component after visual inspection by an automatic application.

6. The method of claim 2 wherein the repair alloy is applied to the surface of the component after fluorescent inspection by a manual application.

7. The method of claim 2 wherein the repair alloy is applied to the surface of the component after fluorescent inspection by an automatic application.

8. The method of claim 1 wherein the step of fluorescent penetrant inspecting under ultraviolet light includes utilizing a CCD camera programmed to detect and distinguish bright areas requiring repair and illuminated by penetrant irradiated by the ultraviolet light from dark areas not requiring repair.

9. The method of claim 8 wherein the step of applying repair alloy to the article to preselected areas requiring repair includes automatically positioning a device that contains the repair alloy over preselected areas requiring repair in response to signals generated by the CCD camera and automatically applying repair alloy to the preselected areas requiring repair in response to signals generated by the CCD camera.

10. The method of claim 1 wherein the step of placing the article in an elevated temperature environment includes heating the article to a temperature of at least about 1800° F.

* * * * *